United States Patent [19]

Heuckeroth et al.

[11] Patent Number: 5,073,571
[45] Date of Patent: Dec. 17, 1991

[54] METHOD OF INHIBITING VIRUS

[75] Inventors: Robert O. Heuckeroth, St. Louis; Steven P. Adams, St. Charles; Jeffrey I. Gordon, Olivette, all of Mo.

[73] Assignee: Washington University, St. Louis, Mo.

[21] Appl. No.: 402,094

[22] Filed: Sep. 1, 1989

Related U.S. Application Data

[63] Continuation-in-part of Ser. No. 208,192, Jun. 16, 1988, which is a continuation-in-part of Ser. No. 151,774, Feb. 3, 1988, abandoned.

[51] Int. Cl.$^5$ ............................................. A01N 37/00
[52] U.S. Cl. ...................................... 514/557; 514/558
[58] Field of Search ................................. 514/558, 557

[56] References Cited

U.S. PATENT DOCUMENTS

| | | | |
|---|---|---|---|
| 4,513,005 | 4/1985 | Baker et al. | 514/451 |
| 4,709,012 | 11/1987 | Adams et al. | 530/328 |
| 4,740,588 | 4/1988 | Adams et al. | 530/328 |

FOREIGN PATENT DOCUMENTS 7407101  1/1974  France.

OTHER PUBLICATIONS

Towler and Glaser, Biochemistry 25, 878–84 (1986).
Towler and Glaser, Proc. Natl. Acad. Sci. U.S.A. 83, 2812–2816 (1986).
Towler et al., Ibid. 84, 2708–2712 (1987).
Towler et al., J. Biol. Chem. 262, 1030–1036 (1987).
Towler et al., Ann. Rev. Biochem., 57, 69–99, (1988).
The Merck Index, Tenth Ed., 1983, p. ONR-96.
Pascal and Ziering, J. Lipid Res. 27, 221–224 (1986).
Heuckeroth et al., J. Biol. Chem. 263(5), 2127–2133 (1988).
Aleynikov et al., Kolsk Branch of the USSR Academy of Sciences, May 3, 1961.
Below et al., Zhokh, vol. 1, No. 4, D. I. Mendeleev, Chem. Engineering Institute in Moscow, Apr. 18, 1964.
Heuckeroth et al., Proc. Nat'l. Acad. Sci. U.S.A. 85, 8795–8799 (1988).
Heuckeroth et al., Ibid. 86, 5262–5266 (1989).

*Primary Examiner*—Frederick E. Waddell
*Assistant Examiner*—Russell Travers
*Attorney, Agent, or Firm*—Scott J. Meyer; James W. Williams, Jr.

[57] ABSTRACT

A method of inhibiting viruses by treatment with oxy- and thio-substituted fatty acid analog substrates of myristoylating enzymes is disclosed. These fatty acid analogs contain an oxygen or sulfur in place of a methylene group in a carbon position from 4 to 13 in the fatty acid chain of a $C_{13}$–$C_{14}$ fatty acid or alkyl ester thereof.

9 Claims, 4 Drawing Sheets

METHOD OF INHIBITING VIRUS

CROSS-REFERENCE TO RELATED APPLICATION

This is a continuation-in-part of copending application Ser. No. 07/208,192, filed June 16, 1988, pending which in turn is a continuation-in-part of application Ser. No. 07/151,774, filed Feb. 3, 1988, now abandoned.

BACKGROUND OF THE INVENTION

This invention relates to a method of inhibiting virus and, more particularly, to a method of inhibiting viruses such as retroviruses with oxy- and thio-substituted fatty acid analog substrates of myristoylating enzymes. These are substrates which are useful in the fatty acid acylation of peptides and proteins.

Fatty acid acylation of specific eukaryotic proteins is a well established process which can conveniently be divided into two categories. On the one hand, palmitate ($C_{16}$) is linked to membrane proteins via ester or thioester linkage post-translationally, probably in the Golgi apparatus.

On the other hand, it is known that myristate ($C_{14}$) becomes covalently bound to soluble and membrane proteins via amide linkage early in the protein biosynthetic pathway. In the N-myristoylated proteins, amino-terminal glycine residues are known to be the site of acylation.

A variety of viral and cellular proteins have been shown to be thus modified by the covalent attachment of myristate linked through an amide bound to glycine at their amino termini. An example of a most thoroughly studied myristoylated protein is the transforming protein (tyrosine kinase) of Rous sarcoma virus, $p60^{v-src}$.

The myristoylation reaction can be represented as follows:

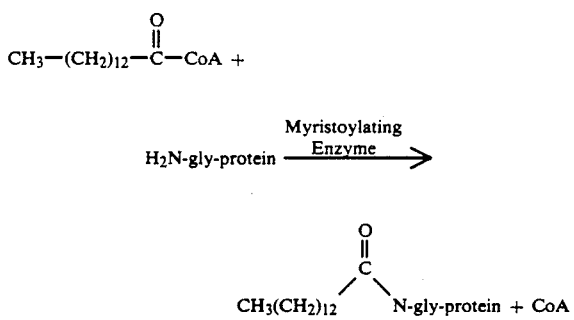

Further background information on the above protein fatty acid acylation can be had by reference to the following series of articles by scientists associated with the Washington University School of Medicine:

Towler and Glaser, *Biochemistry* 25, 878-84 (1986);
Towler and Glaser, *Proc. Natl. Acad. Sci. USA* 83, 2812-2816 (1986);
Towler et al., *Proc. Natl. Acad. Sci. USA* 84, 2708-2712 (1987);
Towler et al., *J. Biol. Chem.* 262, 1030-1036 (1987); and
Towler et al., *Ann. Rev. Biochem.* 57, 69-99 (1988).

Unique synthetic peptides having relatively short amino acid sequences which are useful as substrates of myristoylating enzymes are described in U.S. Pat. No. 4,740,588. Examples of such peptides are Gly-Asn-Ala-Ala-Ala-Ala-Arg-Arg and Gly-Asn-Ala-Ala-Ser-Tyr-Arg-Arg.

Certain other unique synthetic peptides are inhibitors of myristoylating enzymes as described in U.S. Pat. No. 4,709,012.

The present invention is particularly concerned with a method of inhibiting retroviruses such as human immunodeficiency virus (HIV). As such, these fatty acid analog substrates have potential use for the treatment of acquired immune deficiency syndrome (AIDS) and AIDS-related complex (ARC).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4+T-cells (or CD4+cells). See, e.g., Gallo et al., *Science* 224, 500-503 (1984), and Popovic et al., *Ibid.*, 497-500 (1984). This retrovirus has been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [*Ann. Virol. Inst. Pasteur* 135 E, 119-134 (1984)], while HIV-2 was more recently isolated by Montagnier and his co-workers in 1986 [*Nature* 326, 662 (1987)]. As used herein HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, *Science* 241, 426-432 (1988).

The first drug to be approved by the U.S. Food and Drug Administration (FDA) for treatment of AIDS was Zidovudine, also known under its common name, azidothymidine (AZT). Chemically, this drug is 3'-azido-3'-deoxythymidine. This drug was originally selected as a potential weapon against AIDS because it was shown to inhibit replicaton of the virus *in vitro*. Such *in vitro* tests are useful and virtually the only practical method of initially screening and testing potential anti-AIDS drugs. A serious drawback of AZT, however, is its toxic side-effects. Thus, the search for better anti-AIDS drugs continues.

BRIEF DESCRIPTION OF THE INVENTION

In accordance with the present invention, a method is provided for inhibiting viruses by treatment with fatty acid analog substrates for myristoylating enzymes. The preferred antiviral compounds are oxy- and thio-substituted fatty acid analogs which are useful in the fatty acid acylation of proteins. They contain an oxygen or sulfur in place of a methylene (—$CH_2$—) group in a carbon position from 4 to 13 in the fatty acid chain of a $C_{13}$—$C_{14}$ fatty acid or alkyl ester thereof. The carboxyl carbon atom is defined herein as number 1 based on conventional nomenclature. Preferred alkyl esters of the fatty acid analogs have from 1 to 6 carbon atoms in the alkyl group. The fatty acid chain can be derived from saturated alkanoic acid or unsaturated alkenoic and alkynoic acids.

These fatty acid analog substrate compounds are also useful for studying the regulation of enzyme (acyl transferase) action and the role of N-myristoylation in protein function. They can serve as synthetic substrates for the N-myristoylating enzymes in sources such as yeast, wheat germ lysates and mammmalian cells. These compounds differ in hydrophobicity from myristic acid while maintaining approximately the same chain length. Thus, when incorporated into myristoylproteins, they should alter the acylprotein's subsequent interactions with membranes or with other proteins. See Heuckeroth et al., *J. Biol. Chem.* 263, 2127-2133 (1988). It is believed that fatty acid analog substrate compounds with multiple heteroatom substitutions would have greater reduced hydrophobicity than corresponding analogs with a single heteroatom substitution. See Heuckeroth et al., *Proc. Natl. Acad. Sci. USA* 85, 8795-8799 (1988). Heteroatom substituted fatty acid analogs act as substrates for N-myristoyltransferase (NMT) both *in vitro* and *in vivo*. Such results are shown with mammalian cells, e.g. BC$_3$H1, by Heuckeroth et al., *Proc. Natl. Acad. Sci. USA* 86, 5262-5266 (1989).

Illustrative examples of the antiviral oxy and thio-substituted fatty acid analog substrate compounds useful in the method of this invention are:

A. 11-(Ethylthio)undecanoic acid $CH_3CH_2S(CH_2)_{10}COOH$

B. 11-(Ethoxy)undecanoic acid $CH_3CH_2O(CH_2)_{10}COOH$

C. 5-(Octylthio)pentanoic acid $CH_3(CH_2)_7S(CH_2)_4COOH$

D. 11-(Methoxy)undecanoic acid $CH_3O(CH_2)_{10}COOH$

E. 12-(Methoxy)dodecanoic acid $CH_3O(CH_2)_{11}COOH$

F. 5-(octyloxy)pentanoic acid $CH_3(CH_2)_7O(CH_2)_4COOH$

G. 10-(Propylthio)decanoic acid $CH_3(CH)_2S(CH_2)_9COOH$

H. 10-(Propoxy)decanoic acid $CH_3(CH_2)_2O(CH_2)_9COOH$

I. 11-(1 TM Butoxy)undecanoic acid $CH_3(CH_2)_3O(CH_2)_{10}COOH$

J. 10-(2-Fropynoxy)decanoic acid $HC\equiv CC-H_2O(CH_2)_9COOH$

Alternate nomenclature can be used for the above antiviral oxy- and thio-substituted fatty acid analog substrate compounds. For example, compound A can be named 12-thiamyristic acid; compound B can be named 12-oxymyristic acid but preferably 12-oxamyristic acid; and compound J can be named 11-oxy-13-ynemyristic acid.

In a preferred embodiment of the invention the antiviral oxy- and thio-substituted fatty acid analog substrate compounds are based on saturated $C_{13}$-$C_{14}$ fatty acids as exemplified by compounds A to H, above.

Compound I, which is a fatty acid analog based on a $C_{16}$ saturated fatty acid, is less effective than the analogs based on $C_{13}$-$C_{14}$ fatty acids.

In still another embodiment, illustrated by compound J, above, the antiviral fatty acid analog is based on an ω-unsaturated $C_{14}$ fatty acid. It is believed that results such as obtained with the latter compound also can be achieved with fatty acid analogs based on $\Delta^{9,10}$ cis and $\Delta^{9,10}$ trans unsaturated fatty acids, e.g., 12-thiamyristoleic acid and 12-oxymyristelaidic acid.

The preparation of the antiviral oxy- and thio-substituted fatty acid analog substrate compounds can be carried out by methods analogous to the preparation of mixed ethers by the Williamson synthesis. Thus, an appropriate ω-bromo carboxylic acid can be reacted with an alcoholate or an alkyl thiol to produce, respectively, the oxy-substituted fatty acid ether or the thio-substituted fatty acid ether.

In particular, the compounds useful in the method of the invention can be produced by procedures analogous to the synthesis of heteroatom-substituted analogs of stearic acid as described by Pascal and Ziering, *J. Lipid Res.* 27, 221-224 (1986). Using these methods, the sulfur-containing analogs can be prepared by the condensation of appropriate alkyl thiols and ω-bromo carboxylic acids in the presence of alcoholic base. This can be illustrated by the preparation of compound A, above, as follows:

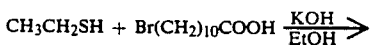

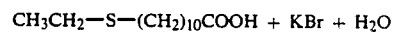

Similarly, the oxygen-containing analogs can be prepared by the reaction of the ω-bromo acids with alcoholic base. This can be illustrated by the preparation of compound E, above, as follows:

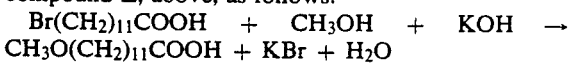

Other antiviral oxy- and thio-substituted fatty acid analog substrate compounds of the invention can be prepared by similar such methods by selecting appropriate alkyl and fatty acid chain lengths in the reactant compounds to produce the desired products. Both of the foregoing type reactions are carried out in organic solvent medium at refluxing temperatures until the desired reaction is essentially complete.

Although specific methods of preparation of the fatty acid analogs are described herein, it will be understood that the antiviral compounds of this invention are not limited to any specific method of preparation.

In a typical antiviral compound of this invention, namely 11-(ethylthio)undecanoic acid, it has been found that introduction of the thioether moiety into the fatty acid chain unexpectedly and surprisingly decreases its hydrophobicity and the hydrophobicity of the respective acyl peptides and fatty acyl proteins, yet leaves intact its ability to act as a substrate for the enzyme myristoyl CoA: protein N-myristoyl transferase (NMT). Purification and use of this enzyme are described, for example, by Towler et al., *Proc. Natl. Acad. Sci. USA* 84, 2708-2712 (1987); *J. Biol. Chem.* 262, 1030-1036 (1987).

The method of inhibiting virus with these fatty acid analogs is illustrated herein by inhibition of two retroviruses, namely the human immunodeficiency virus-1 (HIV-1) and the Maloney murine leukemia virus (MoMLV). Both of these viruses depend on N-myristoylation of their gag polyprotein precursor for assembly.

DETAILED DESCRIPTION OF THE INVENTION

Figure 1A:
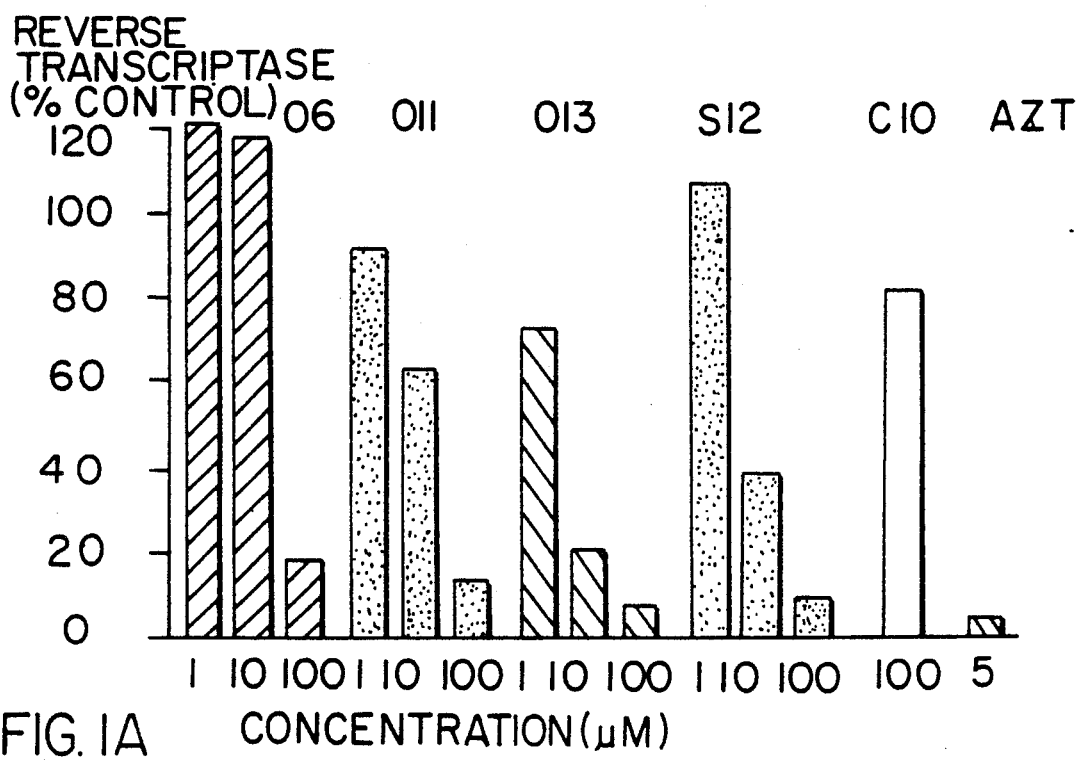

While the specification concludes with claims particularly pointing out and distinctly claiming the subject matter regarded as forming the present invention, it is believed that the invention will be better understood from the following detailed description taken in conjunction with the accompanying drawings in which:

FIG. 1 is a graphical representation which shows the effect of oxygen- and sulfur-substituted analogs of myristic acid on replication of HIV-1 in H-9 cells. Panel A - H9 cells were acutely infected with HIV-1 and treated with 12-(methoxy)dodecanoic acid (13-oxamyristic acid, O13), 10-(propoxy)decanoic acid (11-oxamyristic acid, O11), 5-(octyloxy)pentanoic acid (6-oxamyristic acid, O6) or 11-(ethylthio)undecanoic acid (12-thiamyristic acid, S12) or decanoic acid at the indicated concentrations in serum containing media for 8-10 days. Media was changed every other day. The effect of these compounds on virus production was determined by measuring the reverse transcriptase (RT) activity in samples of the cell culture supernatants. Azidothymidine (AZT) at 5 $\mu$M was used as a positive control. Negative controls consisted of no additions or 0.1ethanol. The results of duplicate assays were averaged. Panel B -Concentration-dependent effects of 13-oxamyristic acid on HIV-1 replication as measured by RT activity (percent of untreated control) and the presence of p24 antigen (ng/ml determined by ELISA). Error bars indicate the S.E.M. of assays done in triplicate. Panel C - The effect of 13-oxamyristic acid on syncytia formation using an arbitrary scale described under Materials and Methods, Example 16, below. Panel D - Toxicity of 13-oxamyristic acid determined by viable cell count (trypan blue exclusion), as well as by [$^3$H]thymidine and [$^3$H]leucine labeling (see under Materials and Methods, Example 16, below). The incorporation of these radiolabeled compounds was determined in the total cell population contained in a well after 10 days of treatment with the analog. Duplicate assays were performed and the results averaged.

FIG. 2 is a graphical representation which shows the effect of oxygen substituted analogs of myristic acid on MoMLV replication. Panel A -Schematic representation of the MoMLV assay system. The circle at the left of the diagram shows the LZ1 virus producing cell that contains (i) a stably integrated packaging mutant of MoMLV designated pMOV-$\Psi$ which has a 350 bp deletion between the 5' splice acceptor site for env and the initiator Met codon (AUG) of Pr65$^{gag}$ and (ii) a second integrated, recombinant DNA sequence with these missing packaging sequences plus the E. coli LacZ gene downstream from an SV40 promoter. This cell produces infectious, replication defective virus (designated LZ1) which carries the LacZ gene. When NIH3T3 cells are exposed to supernatant taken from the LZ1 virus producing cells, they are initially infected and their progeny are detectable by histochemical staining for $\beta$-galactosidase. Thus, the titer of the virus produced by the LZ1 cells after treatment with the various agents, can be readily determined by counting the number of blue NIH3T3 cells. Replication competent MoMLV is not detected using this assay system since the lacZ gene product is not present. Panel B - The effect of 6-oxamyristic acid and 13-oxamyristic acid on LZ1 virus production. The results represent the mean (+1 standard deviation) of three independent tests each done in duplicate. Panel C - Number of viable LZ1 producing cells at the end of a 2 day treatment with analog as measured by trypan blue exclusion. The results of duplicate assays were averaged. Panel D - The effects of analog treatment on incorporation of [$^3$H]leucine. Cells in duplicate wells were pulse labeled for 4 h following three days of incubation with analog or ethanol (0.1%). Duplicate assays were performed. The results were averaged and expressed as a percentage of the results obtained from untreated cells.

The invention is illustrated in greater detail in the following Examples 1 to 11 by the synthesis and testing of representative compounds of the invention as antiviral agents.

EXAMPLE 1

Synthesis of 11-(ethylthio)undecanoic Acid : 11-Bromoundecanoic acid (1 g, 3.77 mmol, Aldrich) was added to a solution of ethanethiol (0.279 mL, 3.77 mmol, Aldrich) and potassium hydroxide (0.486 g, 8.66 mmol) in absolute ethanol (40 mL) and refluxed for 5 hr under a nitrogen atmosphere. After cooling and acidification with HCl, solvent was removed under reduced pressure to give a white solid. The solid was dissolved in ethyl acetate and extracted with water. The organic phase was dried over sodium sulfate, filtered and the solvent removed under reduced pressure. The product was purified by silica column chromatography using increasing concentrations of ethyl acetate in hexane for elution. The product eluted at 25% ethyl acetate/hexane. Solvent was removed under reduced pressure to yield 11-(ethylthio)-undecanoic acid (76 mg, 8%), mp 58-61° C.; $^1$H NMR (300 MHz, CDCl$_3$) $\delta$ 1.24 (t, 3H, J=7.4, CH$_3$), 1.20-1.40 (bm, 12H, methylene envelope), 1.48-1.67 (bm, 4H, S-CH$_2$-CH$_2$ COO-CH$_2$-CH$_2$), 2.33 (t, 2H, J=7.5, CH$_2$-COOH), 2.49 (t, 2H, J=7.4, S-CH$_2$-CH$_2$), 2.51 (q, 2H, J=7.4, S-CH$_2$ -CH$_2$), 10.5 (br, 1H, COOH); $^{13}$C NMR (75.4 MHz, CDCl$_3$) $\delta$ 14.88, 24.70, 25.98, 28.97, 29.08, 29.24*, 29.38, 29.48, 29.69, 31.73, 34.11, 180.05; MS, m/z 246 (M$^+$, 50), 217 (COOH(CH$_2$)$_{10}$S$^+$, 7), 199 (100), 181 (7), 167 (7), 149 (6), 117 (7), 101 (9), 97 (9), 87 (14), 83 (18), 75 (54), 69 (29), 62 (18), 55 (37).

EXAMPLE 2

Synthesis of 11-(ethoxy)undecanoic acid: 11-bromoundecanoic acid (2.25 g, 8.47 mmol) was added to a solution of potassium hydroxide (2.15 g, 38.3 mmol) in absolute ethanol (20 mL) and refluxed for 7 hrs. After cooling and acidification with HCl, solvent was removed under reduced pressure to give a white solid. The sample was dissolved in ethyl acetate and extracted with water. The organic phase was dried over sodium sulfate, and the solvent was removed under reduced pressure. The product was purified by silica column chromatography in 1% diethyl ether/0.3% formic acid/methylene chloride. Solvent was removed under reduced pressure to yield 11-(ethoxy)undecanoic acid (680 mg, 35%): mp 44-45.5° C.; $^1$H NMR (300 MHz, CDCl$_3$) $\delta$ 1.20 (t, 3H, J=7.0, CH$_3$), 1.24-1.40 (bm, 12H, methylene envelope), 1.52-1.68 (bm, 4H, O-CH$_2$-CH$_2$; CH$_2$-CH$_2$-COOH), 2.34 (t, 2H, J=7.5, CH$_2$-COOH), 3.41 (t, 2H, J=6.8, O-CH$_2$-CH$_2$), 3.48 (q, 2H, J=7.0, O-CH$_2$-CH$_3$), 10.25 (br, 1H, COOH); $^{13}$C NMR (75.4 MHz, CDCL$_3$) $\delta$ 15.27, 24.75, 26.23, 29.11, 29.26, 29.40, 29.55*, 29.80, 34.12, 66.06, 70.76, 179.71; m/z 231 (M+H$^+$).

EXAMPLE 3

A Synthesis of Methyl 6-thiotetradecanoate: n-Butyllithium (8.3 mL, 22.1 mmol) was added dropwise to a solution of octanethiol (1; 2.9 g, 19.8 mmol) in dry THF (198 mL) at 0° C. After stirring at 0° C. for 30 min, a solution of methyl 5-bromopentanoate (2; 4.2 g, 21.6 mmol) in dry THF (43 mL) was added dropwise and the resulting heterogeneous mixture was stirred overnight at room temperature. The mixture was concentrated and the residue was partitioned between ether and saturated $NH_4Cl$. After extracting the aqueous layer a second time with ether, the combined organic extracts were washed with brine, dried ($MgSO_4$) and concentrated. Purification by reduced pressure distillation (140–145° C. at 2 mmol) afforded 4.4 g (86%) of the title product. $^1$H-NMR data, δ 3.63 (s, 3H, $OCH_3$); 2.48 (q, 4H, J=6.8 Hz, $CH_2$-S-$CH_2$); 2.30 (t, J-7.0 Hz, $CH_2CO_2CH_3$); 1.78–1.48 (bm, 6H, $CH_2$'s beta to thio and ester moieties); 1.43–1.15 (bs, 10H, $CH_2$'s); 0.85 (t, J=6.6 Hz, $CH_3$); $^{13}$C-NMR data: δ 173.7, 51.4, 33.5, 32.1, 31.7, 31.6, 29.6, 29.1 (2), 29.0, 28.8, 24.1, 22.5, 14.0.

B. Synthesis of 5(Octylthio)pentanoic acid:

NaOH (1.24 g, 31.0 mmol) was added to a solution of methyl 6-thiotetradecanoate (4.25 g, 16.3 mmol) in dry methanol (55 mL) and the resulting mixture brought to reflux. After 5 h the reaction was cooled to room temperature, diluted with 100 ml of water and acidified with 1 M HCl to a pH of 3. This acidified solution was extracted with ether (2X) and the combined organic extracts were washed in water (2X), brine (2X), dried ($MgSO_4$) and concentrated. Column chromatography (ethyl acetate - pentane, 1:9) of the residue afforded 1.4 g, 35% of product. H-NMR data, δ 2.46 (q, 4H, J=7.6 Hz, $CH_2SCH_2$); 2.33 (t, 2H, J=7.2 Hz, $CH_2CO_2H$); 1.75–1.45 (bm, 6H, $CH_2$'s beta to thio and acid moieties); 1.38–1.15 (bs, 10H, $CH_2$'s); 0.83 (t, 3H, J=6.6 Hz, $CH_3$); $^{13}$C-NMR data, 179.4, 33.5, 32.1, 31.8, 31.6, 29.7, 29.1 (2), 28.9 (2), 23.8, 22.6, 14.0; m/z (E1): 246, 145 (100%), 115, 101, 88, 69.

EXAMPLE 4

Synthesis of 11-(methoxy)undecanoic acid:

11-bromoundecanoic acid (10.0 g, 37.7 mmol) was added to a solution of potassium hydroxide (24.3 g, 433 mmol) in methanol (280 mL) and refluxed for 5 hrs. After cooling and acidification with HCl, solvent was removed under reduced pressure. The sample was dissolved in ethyl acetate and extracted with water. The organic phase was dried over sodium sulfate, and the solvent removed under reduced pressure. The product was purified by silica column chromatography using increasing concentrations of ethyl acetate in hexanes for elution. The product eluted in 25% ethyl acetate in hexanes. Solvent was removed under reduced pressure to give 11-(methoxy)undecanoic acid (200 mg, 2.5%): mp 31–32° C.; $^1$H NMR (300 MHz, $CDCl_3$) δ 1.1–1.3 (bm, 12H, methylene envelope). 1.45–1.63 (bm. 4H, O-$CH_2$—$CH_2$, $CH_2$—$CH_2$—COOH), 2.34 (t, 2H, J=7.3, $CH_2$—COOH), 3.45 (s, 3H, $CH_3$), 3.50 (t, 2H, J=6.8, O—$CH_2$), 10.70 (br, COOH); $^{13}$C NMR (75.4 MHz, $CDCl_3$) δ 24.64, 26.00, 29.00, 29.16, 29.29, 29.40, 34.00, 58.23, 72.81, 179.17; m/z 216 (M+).

EXAMPLE 5

Synthesis of 12-(methoxy)dodecanoic acid:

12-bromododecanoic acid (2.0 g, 7.16 mmol) was added to a solution of potassium hydroxide (1.61 g, 28.65 mmol) in methanol (30 mLs) and refluxed for 20 hrs. After cooling and acidification with HCl, solvent was removed under reduced pressure. The sample was dissolved in ethyl acetate and extracted with water. The organic phase was dried over sodium sulfate, and the solvent removed under reduced pressure. The product was purified by silica column chromatography in 1% diethyl ether/0.3% formic acid/methylene chloride to yield 12-(methoxy)dodecanoic acid (640 mg, 39%): mp 45–47° C.; $^1$H NMR (300 MHz, $CDCl_3$) δ 1.20–1.45 (bm, 15H, methylene envelope), 1.51–1.69 (bm, 4H, O-$CH_2$—$CH_2$, $CH_2$—$CH_2$—COOH), 2.34 (t, 2H, J=7.4, $CH_2$—COOH), 3.34 (s, 3H, O-$CH_3$), 3.38 (t, 2H, J=6.7, O—$CH_2$), 10.99 (br, 1H, COOH); $^{13}$C NMR (75.4 MHz, $CDCl_3$) δ 24.75 26.16, 29.10, 29.27, 29.38, 29.44, 29.53, 34.12, 58.50, 72.97, 179.70; m/z 231 (M+H+).

EXAMPLE 6

Synthesis of S-(octyloxy)pentanoic acid:

5-bromopentanoic acid (2g, 11.0 mmol) was added to a solution of potassium hydroxide (2.48 g, 44.2 mmol) in 1-octanol (20 mL) and stirred at 97° C. for 27 hrs. After cooling, the product was extracted at pH=1 with ethyl acetate and water. The organic phase was dried over sodium sulfate and solvent was removed. 1-octanol was removed by short path (Kugelrohr) distillation (50–70° C., 0.5 mm Hg). To ensure complete cleavage of the octyl ester, the residue was stirred 3 hrs with methanol/water/KOH (50%/50%/2.5 g, 40 mL) at 25° C. 1-octanol was extracted into ethyl acetate at pH=12. 5-(octyloxy)pentanoic acid was extracted from the aqueous phase into ethyl acetate after adjusting the pH to 1.5 with HCl. After drying over sodium sulfate, the solvent was removed at reduced pressure. Silica column chromatography in 10% ethyl acetate/ hexane/0.3% formic acid, yielded 5-(octyloxy)pentanoic acid (235 mg, 9%): mp <30° C.; $^1$H NMR (300 MHz, $CDCl_3$) δ 0.88 (t, 3H, J=6.6), 1.18–1.39 (bm, 10H, methylene envelope), 1.48–1.77 (bm, 6H, $CH_2CH_2OCH_2CH_2$, $CH_2CH_2COOH$), 2.39 (t, 2H, J=7.1, $CH_2COOH$), 3.34–3.49 (bm, 4H, $CH_2OCH_2$), 10.66 (br, 1H, COOH); $^{13}$C NMR (75.4 MHz, $CDCl_3$) 14.18, 21.59, 22.73, 26.22, 29.03, 29.32, 29.51, 29.72, 31.89, 33.85, 70.22, 71.07, 179.55; m/z 231 (M+H).

EXAMPLE 7

Synthesis of 10-(propylthio)decanoic acid: 10-bromodecanoic acid (1.0 g, 3.98 mmol) was added to a solution of potassium hydroxide (0.893g, 15.9 mmol) in 1-propanethiol (30 mL) and methanol (30 mL) and stirred at 69° C for 18 hrs. The reaction was allowed to cool to room temperature after the addition of 20 mL water. After acidification to pH=1 and extraction into ethyl acetate, the organic phase was dried over sodium sulfate and solvent removed at reduced pressure to yield a white crystalline powder. The product was purified by silica column chromatography in 8% ethyl acetate/hexane/0.3% formic acid and recrystallization from hexane to yield 10-(propylthio)decanoic acid (210 mg, 21%), mp 42–43.5° C.; $^1$H NMR (300 MHz, $CDCl_3$) δ 0.96 (t, 3H, J=7.3, $CH_3$) 1.15–1.40 (bm, 10H, methylene envelope), 1.49–1.64 (bm, 6H, $CH_3CH_2CH_2SCH_2CH_2$, $CH_2CH_2COOH$), 2.32 (t, 2H, J=7.6, CH· COOH), 2.40–2.55 (bm, 4H, $CH_3CH_2CH_2SCH_2$), 10.93 (Br, 1H, COOH); $^{13}$C NMR (75.4 MHz, $CDCL_3$) δ 13.64, 23.09, 24.71, 28.96, 29.07, 29.13, 29.24, 29.36, 29.77, 32.16, 34.10, 34.28, 179.98; m/z 247 (M+H).

EXAMPLE 8

Synthesis of 10-(propoxy)decanoic acid:

10-bromodecanoic acid (1g, 3.98 mmol) was added to a solution of potassium hydroxide (0.893g, 15.9 mmol) in n-propanol (30 mL) and stirred at 102° C. for 18 hrs. The reaction was allowed to cool to room temperature after the addition of 20 mL water. After acidification to pH=1 and extraction into ethyl acetate, the organic phase was dried over sodium sulfate and solvent removed at reduced pressure to yield a yellow oil. The product was purified by silica column chromatography in 2% diethyl ether/methylene chloride/0.2% formic acid, and then in 7% ethyl acetate/hexane/0.3% formic acid. Recrystallization from hexane at −20° C. yielded 10-(propoxy)decanoic acid (74 mg, 12%: mp <30° C.; $^1$H NMR (300 MHz, CDCl$_3$) δ 0.91 (t, 3H, J=7.5, CH$_3$), 1.18–1.40 (br, 10H, methylene envelope), 1.48–1.67 (bm, 6H, CH$_3$CH$_2$CH$_2$OCH$_2$CH$_2$, CH$_2$CH$_2$COOH), 2.33 (t, 2H, J=7.4, CH$_2$COOH), 3.31–3.45 (bm, 4H, CH$_2$OCH$_2$), 10.37 (br, 1H COOH); $^{13}$C NMR (75.4 MHz, CDCl$_3$) 10.67, 22.94, 24.72, 26.19, 29.09, 29.22, 29.41, 29.74, 34.11, 70.88, 72.53, 179.69; m/z 231 (M+H).

EXAMPLE 9

Synthesis of 11-(1-butoxy)undecanoic acid: 11-bromoundecanoic acid (2 g, 17.5 mmol) was added to a solution of potassium hydroxide (1.7 g, 30.2 mmol) in 1-butanol (20 mL) and the solution was stirred at 40° C. for 5 hrs. After cooling, the reaction mixture was extracted with ethyl acetate and water at pH =2. The organic phase was then washed with saturated sodium chloride, dried over sodium sulfate, and the solvent was removed under reduced pressure. The product was purified over silica column chromatography in 2–10% ethyl acetate/hexane/0.2% formic acid to yield 11-(1-butoxy)undecanoic acid (336 mg, 17%). mp 29–30.5° C.; $^1$H NMR (300 MHz, CDCl$_3$) δ 0.84–0.96 (t, 3H, J=7.3, CH$_3$), 1.18–1.46 (bm, 14H, methylene envelope), 1.47–1.68 (bm, 6H, CH$_2$CH$_2$OCH$_2$CH$_2$, CH$_2$CH$_2$COOH), 2.31 (t, 2H, CH$_2$COOH); 3.32–3.46 (bm, 4H, CH$_2$OCH$_2$), 11.02 (br, 1H, COOH); $^{13}$C NMR (75.4 MHz, CDCl$_3$ δ 14.02, 19.43, 24.74, 26.21, 29.11, 29.28, 29.35, 29.56, 29.64, 29.76, 31.85, 34.14, 70.63, 70.94, 179.82; m/z 259 (M+H).

EXAMPLE 10

Synthesis of 10-(2-propynoxy)decanoic acid:

Sodium hydride (420 mg, 8.75 mmol) was added to propargyl alcohol (68 mL, 1.17 mol) at 4° C. and stirred for 30 minutes at 25° C. 10-Bromodecanoic acid (2g, 7.96 mmol) was added to this mixture and the reaction was stirred at 98° C. for 48 hrs. The reaction mixture was extracted with water and ethyl acetate at pH 1. After drying the organic phase over sodium sulfate, the solvent was removed at reduced pressure. Product was purified over silica gel chromatography in 7–10% ethyl acetate/hexane/0.3% formic acid and then over a second silica gel column in 1–2.5% ethyl acetate/benzene/0.3% formic acid to yield 10-(2-propynoxy)-decanoic acid (245 mg, 14%). mp <30° C.; $^1$H NMR (300 MHz, CDCl$_3$) δ 1.25–1.42 (br, 10H, methylene envelope), 1.54–1.70 (bm, 4H, OCH$_2$CH$_2$, CH$_2$CH$_2$COOH), 2.35 (t, 2H, J=7.4, CH$_2$COOH), 2.43 (t, 1H, J=2.3, HC≡C), 3.52 (t, 2H, J=6.8, OCH$_2$), 4.14 (d, 2H, J=2.5, C≡CCH$_2$O), 10.42 (br, 1H, COOH); $^{13}$C NMR (75.4 MHz, CDCl$_3$) δ 24.68, 26.06, 29.04, 29.17, 29.35*, 29.46, 34.09, 57.95, 70.22, 74.09, 79.90, 180.02; m/z 227 (M+H).

The following example illustrates the antiviral activity of these fatty acid analog substrates against two retroviruses, namely HIV-1 and MoMLV.

EXAMPLE 11

Materials and Methods

Fatty Acid Analogs. 12-methoxy)dodecanoic acid (13-oxyamyristic acid), 10-(propoxy)decanoic acid (11-oxamyristic acid), 5-(octyloxy)pentanoic acid (6-oxamyristic acid), and 11-(ethylthio)undecanoic acid (12-thiamyristic acid) were prepared by methods described hereinbefore. Purified analogs were characterized by TLC, melting point (when appropriate), $^1$H NMR, $^{13}$C NMR and mass spectroscopy.

Assay for HIV-1 Replication. The human T-lymphoid cell line, H9, was provided by R. D. Gallo (NIH) and maintained in RPMI-1640 medium supplemented with 10% fetal bovine serum, 100 IU/mL penicillin, 100 μg/mL streptomycin an 2 mM L-glutamine. HIV-1 strain HXB2gptX [Fisher et al., Science 233, 655–659 (1986)] was obtained from cultures of chronically infected H9 cells [Popovic et al., Science 224, 497–500 (1984)]< filtered through 0.2 μm Millipore filters and stored at −90° C. The titer of the virus stock was determined by serial dilution using syncytia formation and reverse transcriptase activity (see below) as a measure of infectivity in H9 cells.

Cell-free HIV-1, at a multiplicity of infection (m.o.i.) equal to 0.01–0.001, was added to $10^7$ H9 cells which had been pretreated with 2 μg/ml Polybrene® (hexadimethrene bromide, Sigma). Following a 30 min incubation at 37° C. to absorb the virus, 4 × $10^5$ of virus treated cells in 1 mL of fresh medium (plus 10% fetal calf serum, pencillin and streptomycin) were added to each well of a 24 well tissue culture plate (Falcon), and mixed with an equal volume of serum-free RPMI-1640 medium containing analog. Medium containing 5% serum, antibiotics ± analog was replaced every other day. Each of the heteroatom substituted analogs was prepared as a 100 mM stock solution in 100% ethanol and stored at −90° C. prior to dilution in the serum-free RPMI-1640 medium. The maximum final ethanol concentration reached after dilution of the different analogs in media was 0.1%. Therefore, uninfected and infected H9 cells, treated with or without 0.1% ethanol, were used as controls for each test. Ethanol alone had no demonstrable effects.

Except for the preliminary screening of the various (coded) analogs which was done twice, all other assays were performed at least three times. Samples were tested in duplicate each time the assay was repeated.

Virus Assays. Virus was quantitated using supernatant solutions of cells harvested on day 8 (m.o.i.=0.01) or day 10 (m.o.i.=0.001) of treatment. Virions were concentrated 10 fold by precipitation of culture supernatants with a solution of polyethylene glycol (30% in 150 mM NaCl, 0.1 mM phenylmethylsulfonylfluoride). The precipitates were solubilized and virus-associated reverse transcriptase (RT) activity measured by [$^{32}$P]TTP incorporation using a poly(rA)-oligo(dT) template [Poiesz et al., Proc. Natl. Acad. Sci. USA 77, 7415–7419 (1980)]. Cell supernatants were also tested for virus-specific antigen using a p24 ELISA from Dupont (Wilmington, DE). This assay can detect as little as 0.03 ng of antigen/mL (antigen=p24, the major structural nucleocapsid protein of HIV-1, as well as its precursor, Pr55$^{gag}$).

Syncytia Assay. The number of syncytia in each well was determined by microscopic examination on days 4-6 (infected, untreated control cultures), 8 and 10 (analog or decanoate treated cultures). The average number of multi-nucleated giant cells counted per 10 low-power fields (LPF =40 times magnification) was assigned to an arbitrary syncytia scale: 0= <1/LPF, 1+ = 1-4/LPF, 2+ = 5-7/LPF, 3+ = 8-10/LPF, 4+ = >10/LPF. By this criteria uninfected, control cells had zero synctia, and infected, untreated H9 cells were consistently scored as 4+.

Assay of the Effects of Analogs on the Replication of Maloney Murine Leukemia Virus. The LZ1 titer assay was developed for rapid histochemical quantitation of infectious virus production. In brief, the LZ1 virus-producing cell line was derived by Sanes et al., EMBO J. 5, 3133-3142 (1986), from the Ψ-2 cell line. Ψ-2-cells are NIH 3T3 cells that contain a stably integrated packaging mutant (pMOV-Ψ-) of MoMLV. This mutant has a deletion of 350 nucleotides between the 5' donor splice site for env and the initiator methionine codon for Pr65$^{gag}$ [Mann et al., Cell 33, 153-159 (1983)]. The LZ1 cell line is a subclone of Ψ-2 cells that were co-transfectd with pM-MuLV-SV-LacZ [Sanes et al., supra.]and pSVTK neoB and then selected for G418 (Geneticin ®) antibiotic resistance and production of defective MoMLV containing the E. coli β-galactosidase gene [Sanes et al., supra.]. The recombinant virus produced by LZ1 cells is capable of primary infection of NIH 3T3 cells but is replication defective [Sanes et al., surpa.]. Infected NIH 3T3 containing the lac-Z gene can be identified by histochemical staining for β-galactosidase activity.

To assess the effects of analog treatment on MoMLV replication, 1 × 10$^5$ LZ1 producing cells were added to each well of a 24-well tissue culture plate in 1 mL of Dulbecco's Modified Eagle's medium (DME) containing calf serum (final concentration =10%), penicillin (100 IU/mL), streptomycin (100 µg/mL) with or without analog (10-100 µM). After 24 h, the media was removed and fresh serum-containing media ±analog was added. The next day (48 hours after plating), the virus containing supernatant was removed and passed through a 0.2 µm filter. Various size aliquots (25-100 µL of the 1 mL filtrate) were added to 1 × 10$^4$ NIH 3T3 cells contained in 1 mL of DME/10% calf serum/penicillin/streptomycin. These indicator cells had been plated 24 h earlier in 24 well tissue culture plates. Polybrene (Sigma) was added at the same time as the filtrate so that its final concentration was 10 µg/mL. Two days after infection, the NIH 3T3 cells were rinsed with phosphate buffered saline (PBS) and fixed for 5 min at 25° C. in a solution containing PBS, formaldehyde (2%) and glutaraldehyde (2%). Cells were subsequently washed in PBS (two times at 25° C.) and stained for β-galactosidase activity by incubation with a mixture that contained 4-chloro-5-bromo-3-indoyl-β-galactosidase (X-Gal, 1 mg/mL, as per Sanes et al., supra ), potassium ferricyanide (5 mM), potassium ferrocyanide (5 mM), and MgCl$_2$ in PBS. The histochemical reaction mixture was incubated with cells for 6-14 h at 37° C. The total number of β-galactosidase-positive blue cells/well was then determined using a dissecting microscope. Tests were repeated three times with duplicate assays being performed each time. The results obtained after analog treatment were compared to results obtained with cells receiving no additons to the culture media or ethanol (final concentration =0.1%) alone.

Toxicity Studies. These analyses were conducted for both assay systems. Cell survival was determined by trypan-blue exclusion. The number of unstained cells/mL in the treated cultures was divided by the number of unstained cells/mL in the untreated control cultures and expressed as percent control. Protein synthesis was measured at the end of the treatment periods by metabolic labeling for 4 hrs with L-[4,5$^3$H(N)]-leucine (2 µCi/mL media, specific activity =140 Ci/mmol). All cells contained in a given well of a 24 well plate were recovered by scraping, the protein precipitated by TCA (final concentration =10%) and the solution subsequently incubated at 100° C. for 5 min prior to passage over glass fiber filters (Whatman). In the case of the H-9 assay, treated or untreated cells were pulsed labeled at the conclusion of the 10 day incubation. For the MoMLV assay, labeling studies were performed on LZ1 virus producing cells at the conclusion of the 2 day treatment period. An additional control test was performed on NIH 3T3 cells that had never been exposed to virus but which had been incubated with media (± analog) for two days. DNA synthesis was assessed on day 10 of the H9 assay. Cells were labeled for 12 h with [5'-$^3$H]thymidine (0.5 µCi/mL, specific activity =2 Ci/mmol). All the cells in a well were harvested by scraping, their nucleic acid precipitated with TCA (final concentration =10%), and then collected on glass fiber filters prior to counting.

RESULTS

HIV-1 Replication in H9 Cells is Inhibited by Treatment with Heteroatom-Containing Analogs of Myristate. A panel of oxygen and sulfur substituted analogs of myristate were screened above in a double blind fashion for their ability to affect HIV-1 production by the CD4+H-9 human T-lymphoid cell line [Popovic et al., Science 224, 497-500 (1984)]. Cells were exposed to virus as described above and analog (1-100 µM) added 0.5-1 h later. Media containing fetal calf serum ± analog was replaced every other day over a 10 day period. At the conclusion of the treatment period, viral replication was assessed by measuring reverse transcriptase activity.

The results of the double blind drug screen are presented in FIG. 1A. When compared to cultures treated with media alone, media plus ethanol (0.1%) or media containing decanoic acid, it appeared that each of the four analogs reduced HIV-1 production albeit with differing efficacy. 6-oxamyristate was the least effective. No reduction in reverse transcriptase activity (compared to control cultures treated with or without 0.1% ethanol) was noted after a 10 day incubation at analog concentrations ranging from 1 to 10 µM. However, 100 µM 6-oxamyristate reduced reverse transcriptase (RT) activity to 20% of control. More pronounced effects were noted with 1-10 µM 11oxamyristate and 13-oxamyristate as well as 12thiamyristate. 13-Oxamyristate appeared to have the greatest effects -reducing reverse transcription activity to 20% of control at 10 µM and <10% of control at 100 µM. This degree of inhibition was similar to that obtained with 5 µM azidothymidine (AZT) which inhibited viral replication more than 90% in the H9 "acute" assay. By contrast, 100 µM of decanoic acid only reduced RT activity to 80% of control.

Figure 1B:
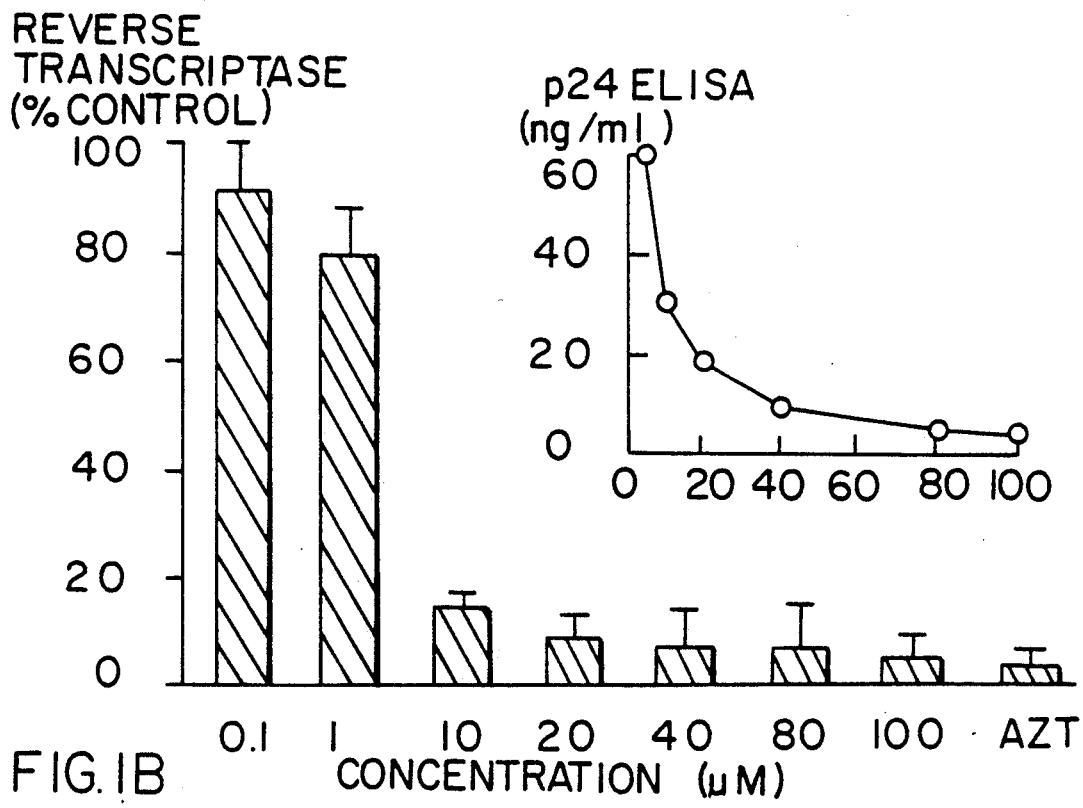
Figure 1C:
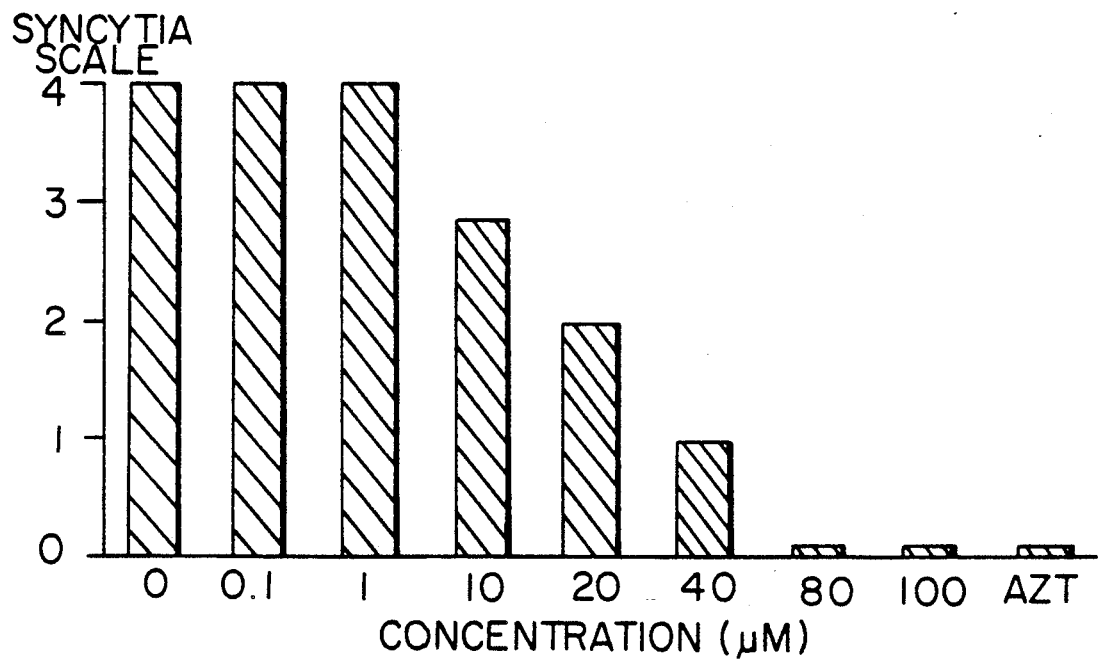

The effect of 13-oxamyristic acid on HIV-1 replication was further evaluated. A dose dependent reduction in reverse transcriptase activity was noted from 0.1 μM to 100 μM (FIG. 1B). In addition, when the amount of virus capsid antigen (p24) was simultaneously measured using an ELISA assay, a similar dose-response was obtained that correlated closely with the results of the reverse transcriptase assay (see inset in FIG. 1B). In both instances, 13-oxamyristate showed a greater than 90% reduction in virus replication in the 20–40 μM range. Syncytia reduction also paralleled the results of the reverse transcriptase and p24 ELISA assays (FIG. 1C). The effect of 13-oxymyristate on syncythia formation likely reflects a reduction in the spread and cytopathicity of HIV-1 in this culture system. The reduction in syncytia by 40–80 μM 13-oxamyristate was comparable to that obtained with 5 μM AZT while decanoic acid or 0.1% ethanol alone had no effect on the number of synctia when compared to infected, untreated H9 controls (FIG. 1C; other data not shown).

Figure 1D:
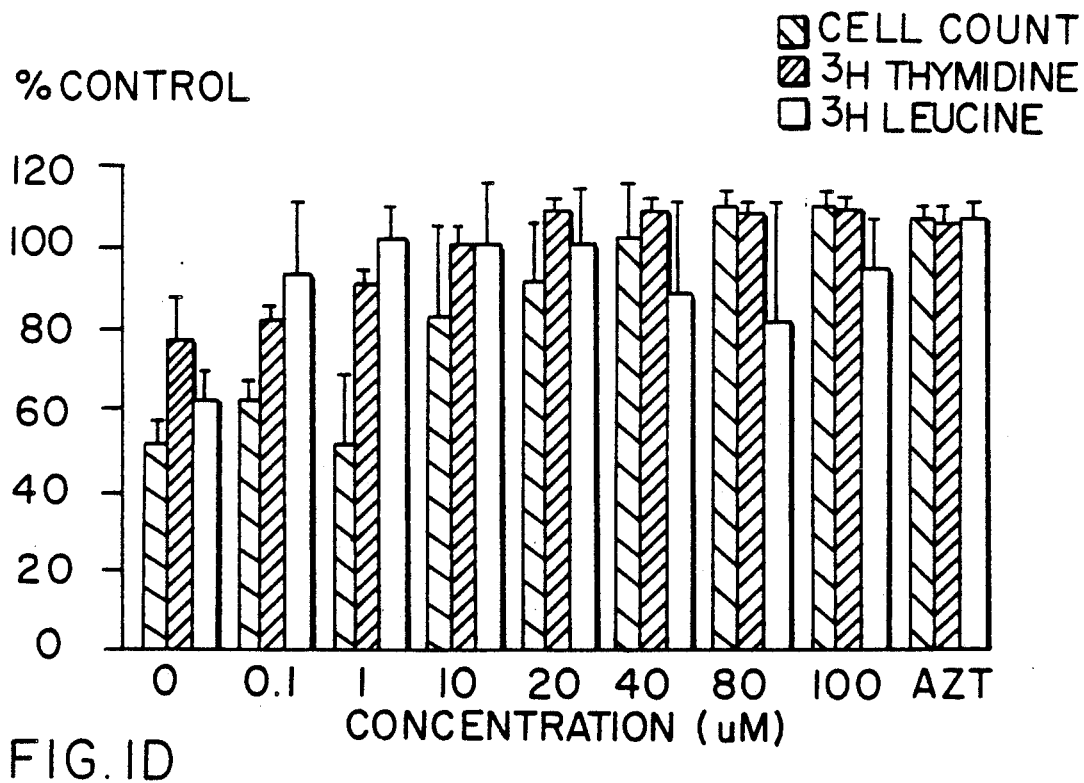

The cellular toxicity of 13-oxamyristate was analyzed using three independent assays of cell viability. First, viable cell number was determined at the conclusion of the 10 day treatment period using trypan blue exclusion. The percentage of living cells in untreated, HIV-1 infected cultures was reduced by 50% compared to that of untreated, uninfected cells (FIG. 1D). This reflects the cytopathic effects encountered with this strain of HIV-1 [Ratner et al., Nature 313, 277–284 (1985)]. When 13-oxamyristate was added to the infected H9 cultures, an increase in viable cell count was observed. Twenty to forty μM analog produced cell counts that were equivalent to that of untreated controls. This "normalization" of viable cell number likely reflects the reduction in infectious virus produced: as virus replication is inhibited, so is the extent of cytopathic effects. This observation also suggested that the analog was not directly toxic to the cells. To further investigate this hypothesis, the effects of increasing concentrations of the analog on DNA and protein synthesis were determined. The results of [$^3$H]leucine and [$^3$H]thymidine labeling correlated with the cell survival data (FIG. 1D). In separate metabolic labeling tests using uninfected H9 cells, 0.1 to 100 μM 13-oxamyristate had no significant effects on growth rates, or protein or DNA synthetic rates. Together these results indicated that the observed effects of 13-oxamyristate on HIV-1 replication were probably not due to nonspecific, deleterious changes in cellular metabolism.

Figure 2A:
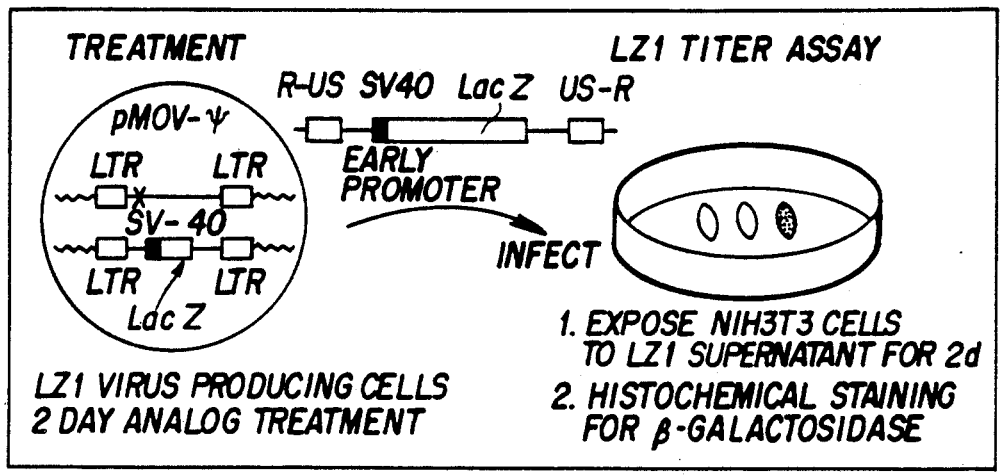
Figure 2B:
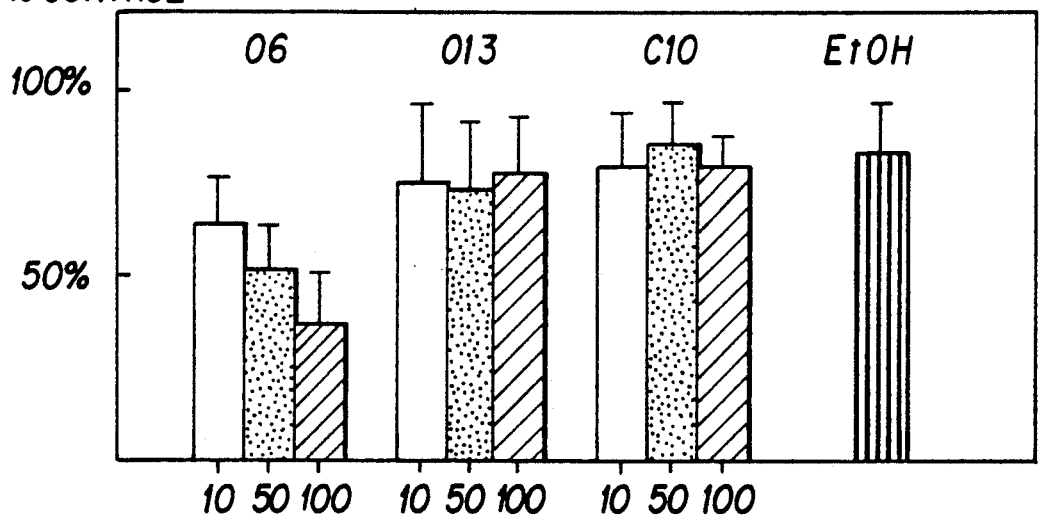

Heteroatom Containing Analogs of Myristate which Effect MoMLV Replication are Different than those that Alter HIV-1 Replication. Two analogs were examined in this assay: 6-oxamyristic acid which was the least effective of the four compounds tested in the HIV-1 replication assay and 13-oxamyristic acid which was the most effective. A novel assay system was developed to assess the effects of these compounds on MoMLV replication. The details of the system are described above and illustrated in FIG. 2A. The LZ1 virus is a derivative of MoMLV which is defective in replication. Once infection has occurred, viral propagation is blocked and the provirus is restricted to the progeny of the initially infected cell. The virus also carries the E. coli LacZ gene which provides a quantitative marker of infectious virus production. In the MoMLV assay system introduced here, LZ1 virus producing cells are treated with the different analogs for 2 days. NIH 3T3 cells are then exposed to aliquots of the filtered media harvested from LZ1 virus producing cells and the resultant foci identified by histochemical staining for β-galactosidase. The effect of drugs on virus replication can be determined by comparing the number of foci (blue cells) produced by filtrates prepared from treated cultures to that produced by untreated controls. As shown in FIG. 2B, 13-oxamyristate had no effect on virus replication in concentrations up to 100 μM. By contrast, 6-oxamyristate, which had no effect on HIV-1 replication, inhibits MoMLV replication in a concentration dependent fashion: a 40% reduction was observed at 10 μM while 100 μM produced an average reduction in virus titers of >60%. Ethanol (0.1%) and decanoic acid (10–100 μM) produced no significant reductions compared to untreated controls.

Figure 2C:
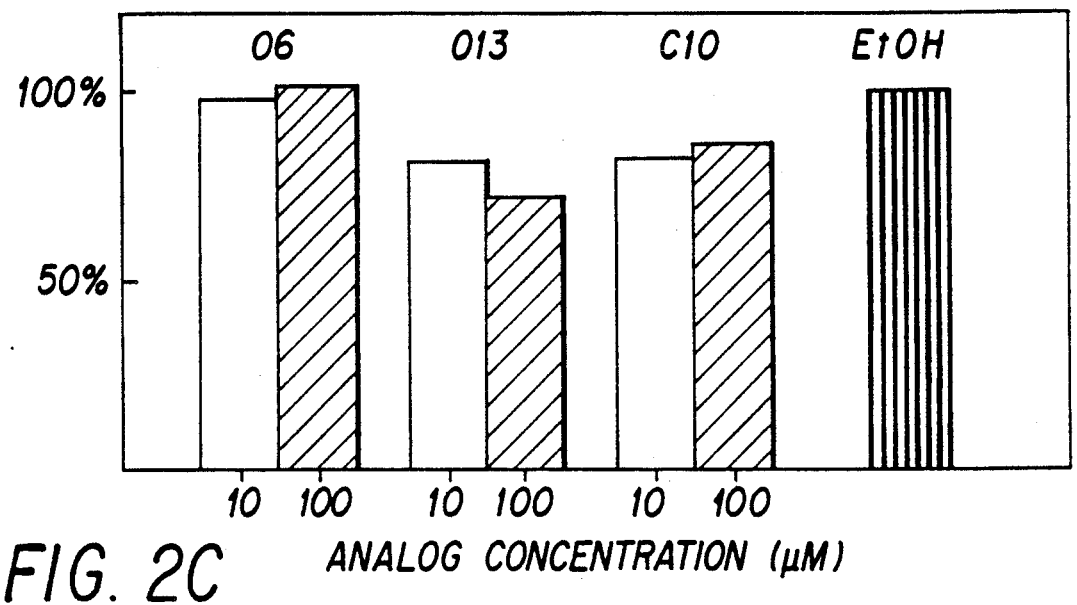
Figure 2D:
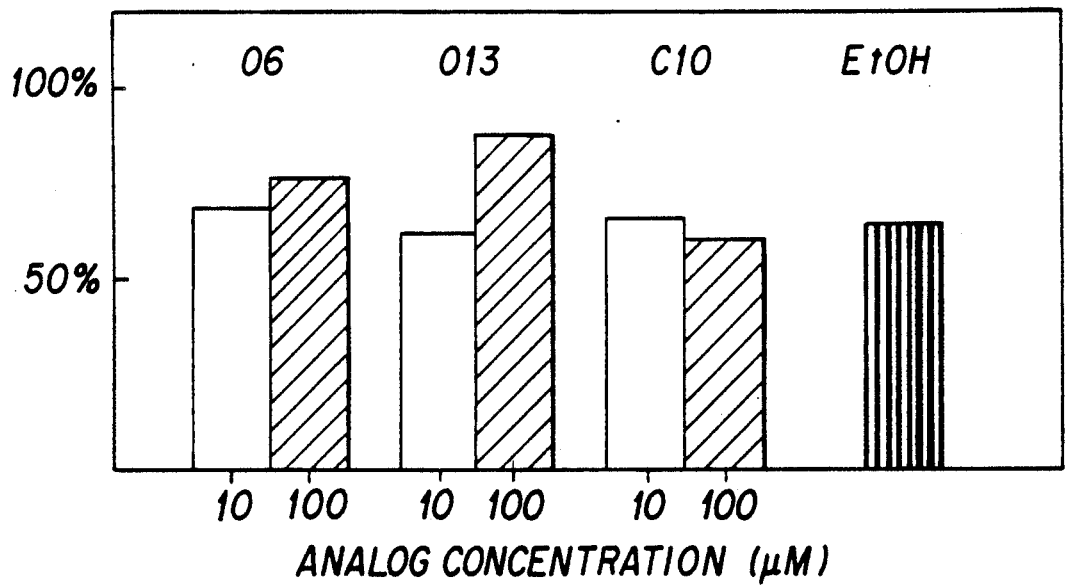

Toxicity studies analogous to those described for the HIV-1 assay system were performed. The number of viable LZ1 virus producing cells as well as the NIH 3T3 "reporters" showed <20% differences between the various treatment groups and untreated controls (FIG. 2C; other data not shown). Pulse labeling studies with [$^3$H]leucine demonstrated a 10–40% reduction in protein synthesis in treated LZ1 cells compared to untreated controls (FIG. 2D). However, this reduction was probably nonspecific since there were no significant differences between cells treated with analogs, 0.1% ethanol or 10–100 μM decanoic acid. [$^3$H]Leucine labelling tests of NIH 3T3 cells treated for 2 days with analog showed no significant (<10%) differences when compared to control cells.

The antiviral agents described herein can be used for administration to mammalian hosts infected with retroviruses and the like by conventional means, preferably in formulations with pharmaceutically acceptable diluents and carriers. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. A suitable route of administration is orally in the form of capsules, tablets, syrups, elixirs and the like, although parenteral administration also can be used. Appropriate formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, PA.

Standard amino acid abbreviations are used below to identify the sequence of the peptides herein as follows:

| Amino Acid | Abbreviation |
| --- | --- |
| L-Alanine | Ala or A |
| L-Arginine | Arg or R |
| L-Asparagine | Asn or N |
| L-Aspartic acid | Asp or D |
| L-Glutamine | Gln or Q |
| L-Glycine | Gly or G |
| L-Leucine | Leu or L |
| L-Lysine | Lys or K |
| L-Proline | Pro or P |
| L-Serine | Ser or S |
| L-Tyrosine | Tyr or Y |
| L-Valine | Val or V |

Various other examples will be apparent to the person skilled in the art after reading the present disclosure without departing from the spirit and scope of the invention. Thus, it will be apparent that various other heteroatom fatty acid analogs will be useful for inhibiting retroviruses and other viruses consistent with the foregoing disclosure. All such other examples are included within the scope of the appended claims.

What is claimed is:

1. The method of inhibiting the replication of virus in a mammalian host infected with said virus comprising administering to said host a virally inhibitory effective amount of an oxy- or thio-substituted fatty acid analog substrate of myristoylating enzymes selected from the group consisting of $C_{13}$ or $C_{14}$ fatty acids or alkyl esters thereof in which a methylene group normally in a carbon position from 4 to 13 is replaced with oxygen or sulfur.

2. The method of claim 1 in which a methylene group is replaced with oxygen in said fatty acid analog.

3. The method of claim 1 in which a methylene group is replaced with sulfur in said fatty acid analog.

4. The method of claim 1 in which the fatty acid in said fatty acid analog is a saturated $C_{13}$ or $C_{14}$ fatty acid.

5. The method of claim 1 in which the virus a retrovirus.

6. The method of claim 5 in which the retrovirus is HIV-1.

7. The method of claim 5 in which the retrovirus is MoMLV.

8. The method of claim 6 in which the fatty acid analog is 12-(methoxy)dodecanoic acid.

9. The method of claim 7 in which the fatty acid analog is 5-(octyloxy)pentanoic acid.

* * * * *

UNITED STATES PATENT AND TRADEMARK OFFICE
CERTIFICATE OF CORRECTION

PATENT NO. : 5,073,571

DATED : December 17, 1991

INVENTOR(S) : Robert O. Heuckeroth, Steven P. Adams and Jeffrey I. Gordon

It is certified that error appears in the above-identified patent and that said Letters Patent is hereby corrected as shown below:

At col. 3, line 49, "11-(1 TM Butoxy)" should read --11-(1-Butoxy)--.
At col. 3, line 51, "10-(2-Fropynoxy)" should read --10-(2-Propynoxy)--.
At col. 7, line 34, "H-NMR" should read --$^1$H-NMR--. At col. 8, line 19, "S-(octyloxy)" should read --5-(octyloxy)--.

Signed and Sealed this

Third Day of August, 1993

Attest:

MICHAEL K. KIRK

Attesting Officer

Acting Commissioner of Patents and Trademarks